United States Patent
Nagai (10) Patent No.: US 10,436,699 B2
(45) Date of Patent: Oct. 8, 2019

(54) ANALYZING SYSTEM AND ANALYZING APPARATUS

(71) Applicant: NIHON KOHDEN CORPORATION, Tokyo (JP)

(72) Inventor: Yutaka Nagai, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/885,432

(22) Filed: Oct. 16, 2015

(65) Prior Publication Data

US 2016/0109353 A1 Apr. 21, 2016

(30) Foreign Application Priority Data

Oct. 20, 2014 (JP) .................................. 2014-213444

(51) Int. Cl.
| | |
|---|---|
| *G01N 33/00* | (2006.01) |
| *G01N 31/00* | (2006.01) |
| *G01N 15/14* | (2006.01) |
| *G01N 27/06* | (2006.01) |
| *G01N 15/10* | (2006.01) |

(52) U.S. Cl.
CPC ..... *G01N 15/1434* (2013.01); *G01N 15/1031* (2013.01); *G01N 15/1468* (2013.01); *G01N 27/06* (2013.01); *G01N 2015/1037* (2013.01)

(58) Field of Classification Search
USPC .............................................. 422/73; 436/10
See application file for complete search history.

(56) References Cited

U.S. PATENT DOCUMENTS

| 5,159,397 A | 10/1992 | Kosaka et al. |
| 5,247,340 A | 9/1993 | Ogino |
| 5,548,395 A | 8/1996 | Kosaka |
| (Continued) | | |

FOREIGN PATENT DOCUMENTS

| JP | H04-270940 A | 9/1992 |
| JP | H04-270961 A | 9/1992 |
| (Continued) | | |

OTHER PUBLICATIONS

David S. Boyle, et al., "Emerging technologies for point-of-care CD4 T-lymphocyte counting" Trends in Biotechnology, Jan. 2012, vol. 30, No. 1.

(Continued)

*Primary Examiner* — Dean Kwak
(74) *Attorney, Agent, or Firm* — Pearne & Gordon LLP (57) ABSTRACT

An analyzing system includes an imaging cytometer having a first imaging section configured to perform an imaging of particles contained in an analyte sample to generate images, the imaging cytometer being configured to analyze the images generated by the first imaging section, and a blood cell analyzing apparatus configured to analyze particles contained in the analyte sample by at least one of an electrical resistance method and an optical analyzing method. One of the imaging cytometer and the blood cell analyzing apparatus has an analyzing section configured to produce a report of an analysis of the analyte sample based on particle information acquired by the imaging cytometer and particle information acquired by the blood cell analyzing apparatus.

10 Claims, 10 Drawing Sheets

(56) References Cited

U.S. PATENT DOCUMENTS

| | | | |
|---|---|---|---|
| 5,548,661 A | 8/1996 | Price et al. | |
| 5,627,037 A * | 5/1997 | Ward | G01N 33/56972 |
| | | | 250/459.1 |
| 5,644,388 A | 7/1997 | Maekawa et al. | |
| 5,825,477 A | 10/1998 | Furuie | |
| 6,229,912 B1 | 5/2001 | Katahira et al. | |
| 2003/0030783 A1* | 2/2003 | Roche | G01N 1/38 |
| | | | 356/39 |
| 2005/0036667 A1 | 2/2005 | So et al. | |
| 2009/0298067 A1* | 12/2009 | Irimia | G01N 33/56966 |
| | | | 435/5 |
| 2010/0090677 A1* | 4/2010 | Britton | G01N 15/1429 |
| | | | 324/71.1 |
| 2011/0089328 A1 | 4/2011 | Li | |
| 2011/0121198 A1 | 5/2011 | Nakata et al. | |
| 2011/0204256 A1 | 8/2011 | Patt | |
| 2012/0021482 A1 | 1/2012 | Zuba-Surma et al. | |
| 2012/0202237 A1* | 8/2012 | Sedoglavich | G01N 15/1404 |
| | | | 435/29 |
| 2014/0212917 A1* | 7/2014 | Durack | G01N 15/1427 |
| | | | 435/34 |
| 2014/0291550 A1* | 10/2014 | Jimenez | G01N 15/1404 |
| | | | 250/459.1 |
| 2015/0050688 A1* | 2/2015 | Thrasher | G01N 15/1425 |
| | | | 435/34 |

FOREIGN PATENT DOCUMENTS

| | | |
|---|---|---|
| JP | H05-79970 A | 3/1993 |
| JP | H06-213797 A | 8/1994 |
| JP | H07-181123 A | 7/1995 |
| JP | H08-029324 A | 2/1996 |
| JP | H08-114540 A | 5/1996 |
| JP | H08-128944 A | 5/1996 |
| JP | H09-072842 A | 3/1997 |
| JP | H09-178644 A | 7/1997 |
| JP | H10-073528 A | 3/1998 |
| JP | H10-132812 A | 5/1998 |
| JP | H10-260132 A | 9/1998 |
| JP | H10-293094 A | 11/1998 |
| JP | H11-511557 A | 10/1999 |
| JP | 2005-121602 A | 5/2005 |
| JP | 2006-126364 A | 5/2006 |
| JP | 2011-048013 A | 3/2011 |
| JP | 2011-112779 A | 6/2011 |
| JP | 2013-502590 A | 1/2013 |
| WO | 97-08523 A1 | 3/1997 |

OTHER PUBLICATIONS

H.J. Tanke, et al., "Combined flow cytometry and image cytometry of the same cytological sample" Journal of Microscopy, Apr. 1983, vol. 130, Pt. 1.

David A. Basiji, et al., "Cellular Image Analysis and Imaging by Flow Cytometry" NIH Public Access, Clinics in Laboratory Medicine Sep. 2007; 27(3): 653-viii.

European Search Report for Application No. EP 15 19 0364 dated Mar. 18, 2016.

Japanese Office Action issued in Patent Application No. JP 2014-213444 dated Dec. 14, 2017.

Japanese Office action issued in Patent Application No. JP-2014-213444 dated Jul. 18, 2018.

Japanese Office Action issued in Patent Application No. JP-2018-022372 dated Jan. 10, 2019.

* cited by examiner

ANALYZING SYSTEM AND ANALYZING APPARATUS

CROSS-REFERENCE TO RELATED APPLICATION(S)

The present application claims priority from Japanese Patent Application No. 2014-213444 filed on Oct. 20, 2014, the entire content of which is incorporated herein by reference.

BACKGROUND

The presently disclosed subject matter relates to an analyzing system and an analyzing apparatus, and in particular, to an analyzing system and analyzing apparatus for analyzing cells or the like.

When cells or the like are to be analyzed, a technique called a cytometry is employed. A cytometry is roughly classified into a flow cytometry and an imaging cytometry.

In a flow cytometry, suspended cells are guided into a sensing zone, and scattered light, fluorescent light, and the like are measured at high speed. In an imaging cytometry, images of cells are taken to analyze the cells.

JPH08-128944A discloses a classifying apparatus, an example of a cytometer, configured to detect backward scattered light in addition to forward scattered light and side scattered light to perform analysis. By detecting the backward scattered light, it is possible to accurately detect cells, even very small cells, and to accurately classify the cells.

In a cytometry, as described above, there are a flow cytometry and an imaging cytometry. A flow cytometry has an advantage that a large amount of cells can be quantitatively analyzed, but has a problem in that detailed information of the cell morphology cannot be obtained. In an imaging cytometry, detailed information of the cell morphology can be obtained, but there is a problem in that it is difficult to obtain a sufficient amount of statistics.

That is, in either of the techniques, it has been difficult to perform an accurate analysis of cells (e.g., acquisition of information which cannot be acquired by a general flow cytometry or a general imaging cytometry alone).

SUMMARY

Illustrative aspects of the present invention provide an analyzing system and analyzing apparatus that can perform an accurate analysis on cells (e.g., acquisition of information which cannot be acquired by a general flow cytometry or a general imaging cytometry alone).

According to an illustrative aspect of the present invention, an analyzing system includes an imaging cytometer having a first imaging section configured to perform an imaging of particles contained in an analyte sample to generate images, the imaging cytometer being configured to analyze the images generated by the first imaging section, and a blood cell analyzing apparatus configured to analyze particles contained in the analyte sample by at least one of an electrical resistance method and an optical analyzing method. One of the imaging cytometer and the blood cell analyzing apparatus has an analyzing section configured to produce a report of an analysis of the analyte sample based on particle information acquired by the imaging cytometer and particle information acquired by the blood cell analyzing apparatus.

According to another illustrative aspect of the present invention, an analyzing system includes a blood cell analyzing apparatus configured to analyze particles contained in an analyte sample by at least one of an electrical resistance method and an optical analyzing method, and an imaging cytometer configured to perform, when the blood cell analyzing apparatus detects an abnormality through the analysis on the analyte sample, imaging of particles contained in the analyte sample to generate images and to analyze the images.

According to another illustrative aspect of the present invention, an analyzing system includes an imaging cytometer configured to performs imaging of particles contained in an analyte sample to generate images and to analyze the images, and a blood cell analyzing apparatus configured to analyze, when the imaging cytometer detects an abnormality through the analysis on the analyte sample, particles contained in the analyte sample by at least one of an electrical resistance method and an optical analyzing method.

According to another illustrative aspect of the present invention, a blood cell analyzing apparatus includes an imaging cytometer configured to perform imaging of particles contained in an analyte sample to generate images and to analyze the images, a measuring section configured to analyze the particle contained in the analyte sample by at least one of an electrical resistance method and an optical analyzing method, and an analyzing section configured to produce a report of an analysis of the analyte sample based on particle information acquired by the imaging cytometer and particle information acquired by the measuring section.

According to the apparatuses described above, advantages of both a flow cytometer and an imaging cytometer can be obtained. More specifically, the imaging cytometer acquires detailed information (the particle measurement value, the particle ratio, and the like) by imaging the particles, and the blood cell analyzing apparatus performs a detailed quantitative analysis. By combining the processings of the two apparatuses, it is possible to acquire detailed information that cannot be acquired by a conventional apparatus and to perform a flexible test.

DETAILED DESCRIPTION

Figure 1:
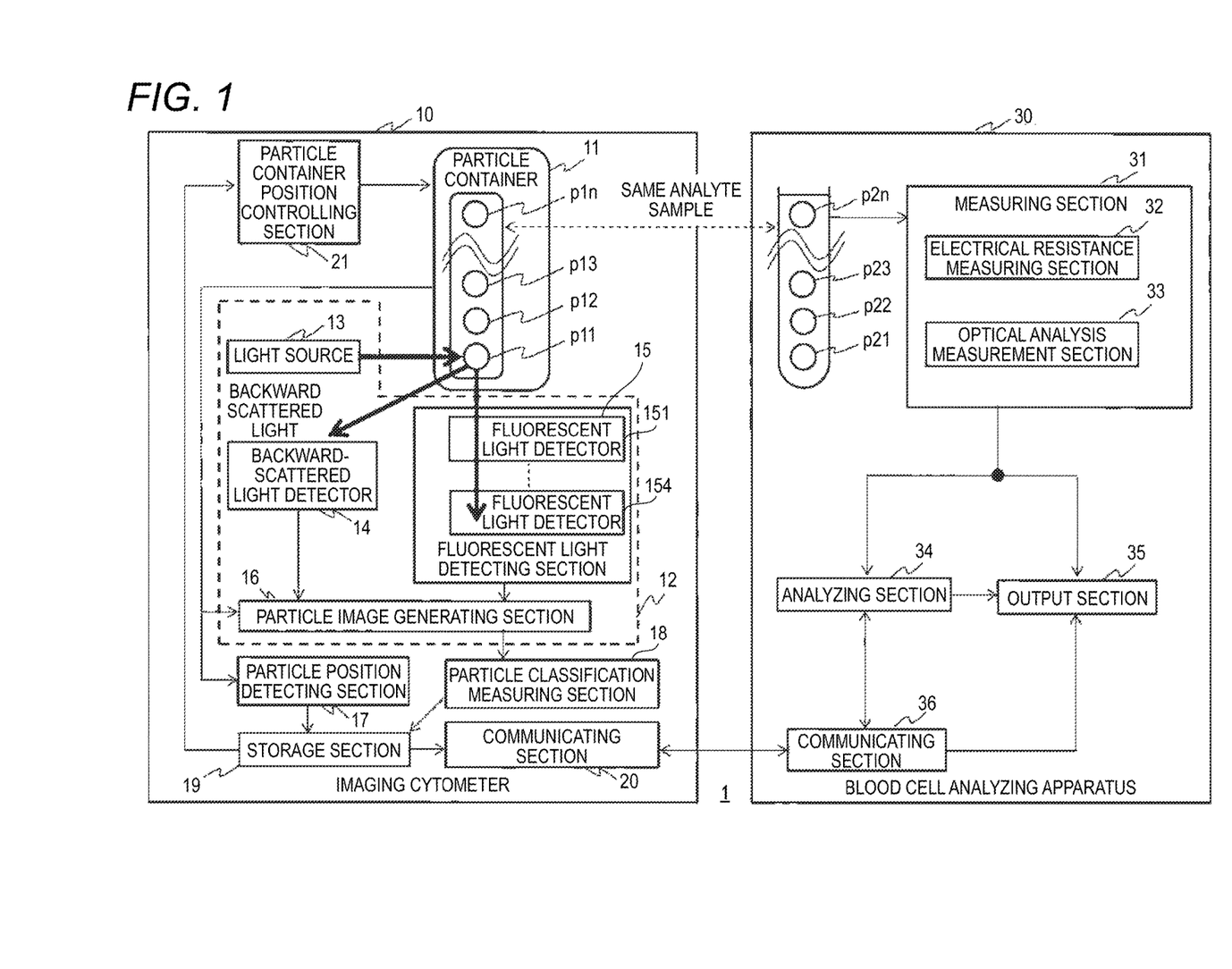
FIG. 1 is a block diagram of a configuration of an analyzing system according to an exemplary embodiment of the present invention.

Hereinafter, exemplary embodiments of the invention will be described with reference to the drawings. FIG. 1 is a block diagram of a configuration of an analyzing system 1 according to an exemplary embodiment of the present invention. The analyzing system 1 has an imaging cytometer 10 and a blood cell analyzing apparatus 30.

The imaging cytometer 10 has a particle container 11, an imaging section 12 (a first imaging section), a particle position detecting section 17, a particle classification measuring section 18, a storage section 19, a communicating section 20, and a particle container position controlling section 21. The imaging cytometer 10 performs an imaging of an analyte sample to generate an image, and analyzation by using the image (specifically, detects the particle ratio, the particle measurement value, and the like). Since the process of imaging a particle is performed, the imaging cytometer 10 cannot analyze a large amount of analyte sample (in other words, it is difficult to ensure a necessary amount of statistics), but has an advantage that detailed information of cell morphology can be obtained.

The particle container 11 is a container which holds the analyte sample (preferably, blood) to be analyzed. Blood cells contain granules or particles (hereinafter, referred to simply as particles) having different sizes depending on the kinds. In the exemplary embodiment, the particle container 11 holds particles p11 to p1n. The use of the imaging cytometer 10 is not particularly limited, but is particularly useful in, for example, analysis of blood containing microparticles. Microparticles are minute membrane endoplasmic reticulums which are released by breaking off a part of the platelet membrane. It has been reported that the detection of microparticles is useful in prediction of a vascular disorder in that the prethrombotic state can be confirmed by the detection of microparticles (see, Inami N, Nomura S, et al, "P-selection and platelet-derived microparticles associated with monocyte activation markers in patients with pulmonary embolism", Clin. Appl. Thromb Hemost, 2003 October; 9(4): 309-16).

The imaging section 12 performs an imaging of a particle in the particle container 11 to image the particle. The configuration of the imaging section 12 is not particularly limited, and, for example, the section may be configured as shown in FIG. 1. In the configuration of FIG. 1, the imaging section 12 includes a light source 13, a backward-scattered light detecting section 14, a fluorescent light detecting section 15, and a particle image generating section 16. The light source 13 irradiates the particle container 11 with laser light. The laser light excites scattered light and fluorescent light. The position of the particle container 11 is controlled during the analysis performed by the imaging cytometer 10. That is, the particle container 11 is moved such that the particles p11 to p1n are irradiated with the laser light during the analysis by the imaging cytometer 10. The control of the position of the particle container 11 will be described later in detail with reference to FIGS. 4A to 5D.

The backward-scattered light detecting section 14 detects the intensity of backward scattered light that is produced when the light source 13 irradiates the particle container 11 with laser light. The characteristics of scattered light, and meaning of the detection of backward scattered light will be briefly described.

In blood cells, granules or particles (hereinafter, simply referred to as particles) having different sizes depending on the kinds are contained. When a particle is irradiated with light, the angular distribution of scattered light is different depending on the size of the particle. Most of scattered light due to a large particle is concentrated forward, and its intensity is proportional to the square of the diameter of the particle (the Fraunhofer diffraction theory). When the particle size (the diameter of the particle) is small, scattered light due to the particle is emitted in every direction, and the intensity of the scattered light is proportional to the sixth power of the diameter of the particle (the Rayleigh criterion). Furthermore, it is known that scattered light due to a small particle is varied in the angular distribution depending on the vibration direction of incident light, and, in the case of a rugged particle, the polarizing phenomenon due to scattering is lost.

When a particle having a diameter d is irradiated with laser light having a wavelength $\lambda$, the particle size parameter $\alpha$ a is represented as $\alpha = \pi d/\lambda$.

Figure 2:
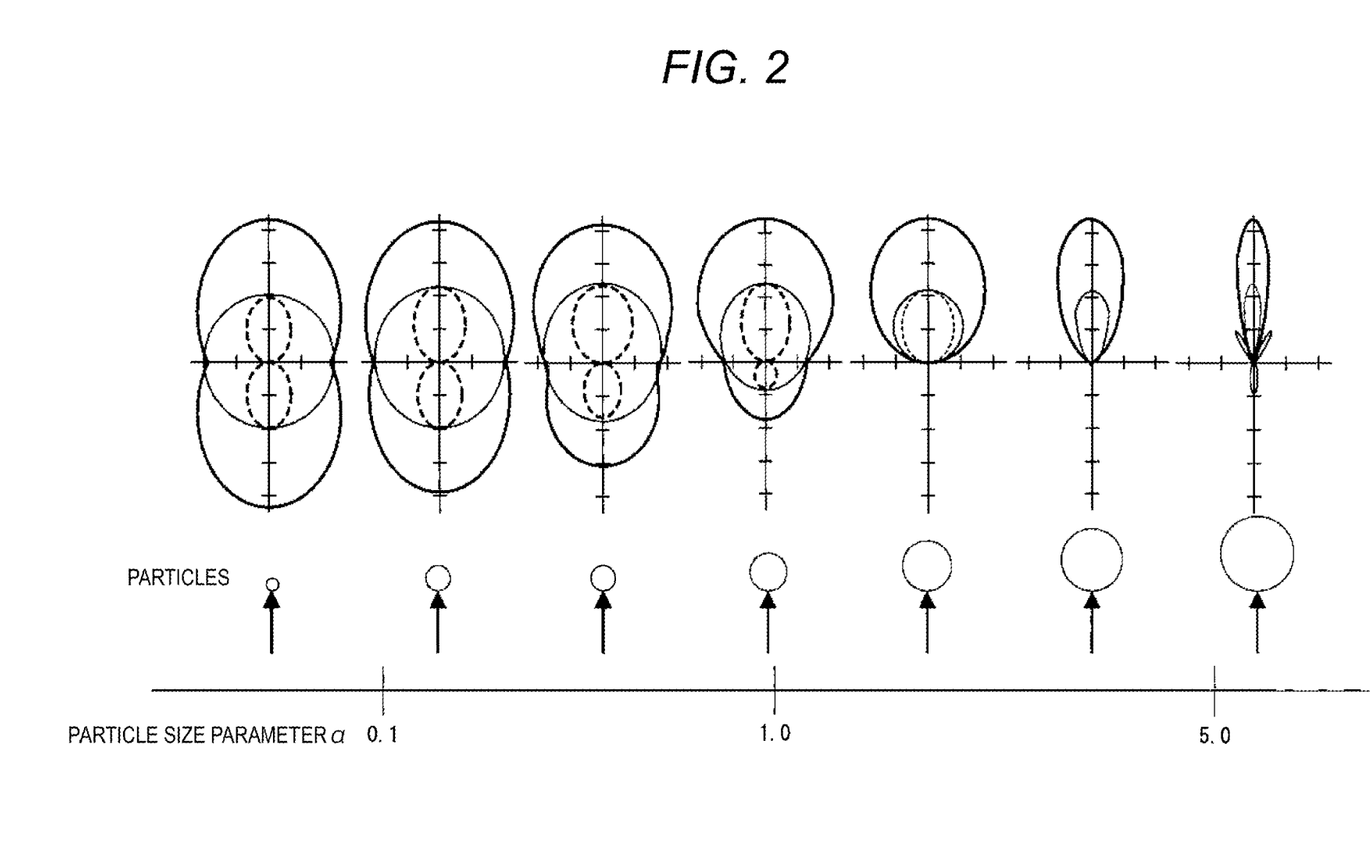
FIG. 2 is a diagram illustrating relationships between a particle size parameter α and patterns of a scattered light component.

FIG. 2 is a diagram showing relationships between the particle size parameter $\alpha$ and patterns of a scattered light component. FIG. 2 shows scattered light patterns in the case where laser light is emitted from the lower side of the drawing in the upward direction. As seen from FIG. 2, as the particle size parameter $\alpha$ varies from a smaller value to a larger value, i.e., the larger the particle size, the backward scattered light component becomes smaller. In other words, the smaller the particle size is, the larger the backward scattered light component becomes. In analysis of a small-size particle such as an above-described microparticle, therefore, an analysis of backward scattered light is very useful.

The relationships between the particle size parameter and scattered light are described in detail in paragraphs 0014 to 0020 of JPH08-128944A.

The backward-scattered light detecting section 14 detects backward scattered light that is produced when the particle container 11 is irradiated with the laser light. The backward-scattered light detecting section 14 may be configured by providing a mirror, a lens, and a detector such as a photodiode (see, e.g., JPH08-128944A). The backward-scattered light detecting section 14 correlates the detected intensity of the backward scattered light with position information (e.g., the x- and y-coordinates) indicating the position of irradiation of the laser light, and then supplies the intensity and the information to the particle image generating section 16.

The fluorescent light detecting section 15 is configured by a plurality of fluorescent light detectors 151 to 154. The fluorescent light detectors 151 to 154 detect fluorescent light which is excited by the laser light, in accordance with the kind The fluorescent light detecting section 15 correlates the fluorescent light intensities detected by the fluorescent light detectors 151 to 154, with the position information (x- and y-coordinates) indicating the position of irradiation of the laser light, and then supplies the intensity and the information to the particle image generating section 16.

The particle image generating section 16 receives the scattered light intensity information correlated with the position information (x- and y-coordinates), and the fluorescent light intensity information correlated with the position information (x- and y-coordinates). Based on the information, the particle image generating section 16 generates an image (particle image) indicating the shape of a particle contained in the analyte sample. A method of generating the particle image will be described with reference to FIG. 3.

Figure 3:
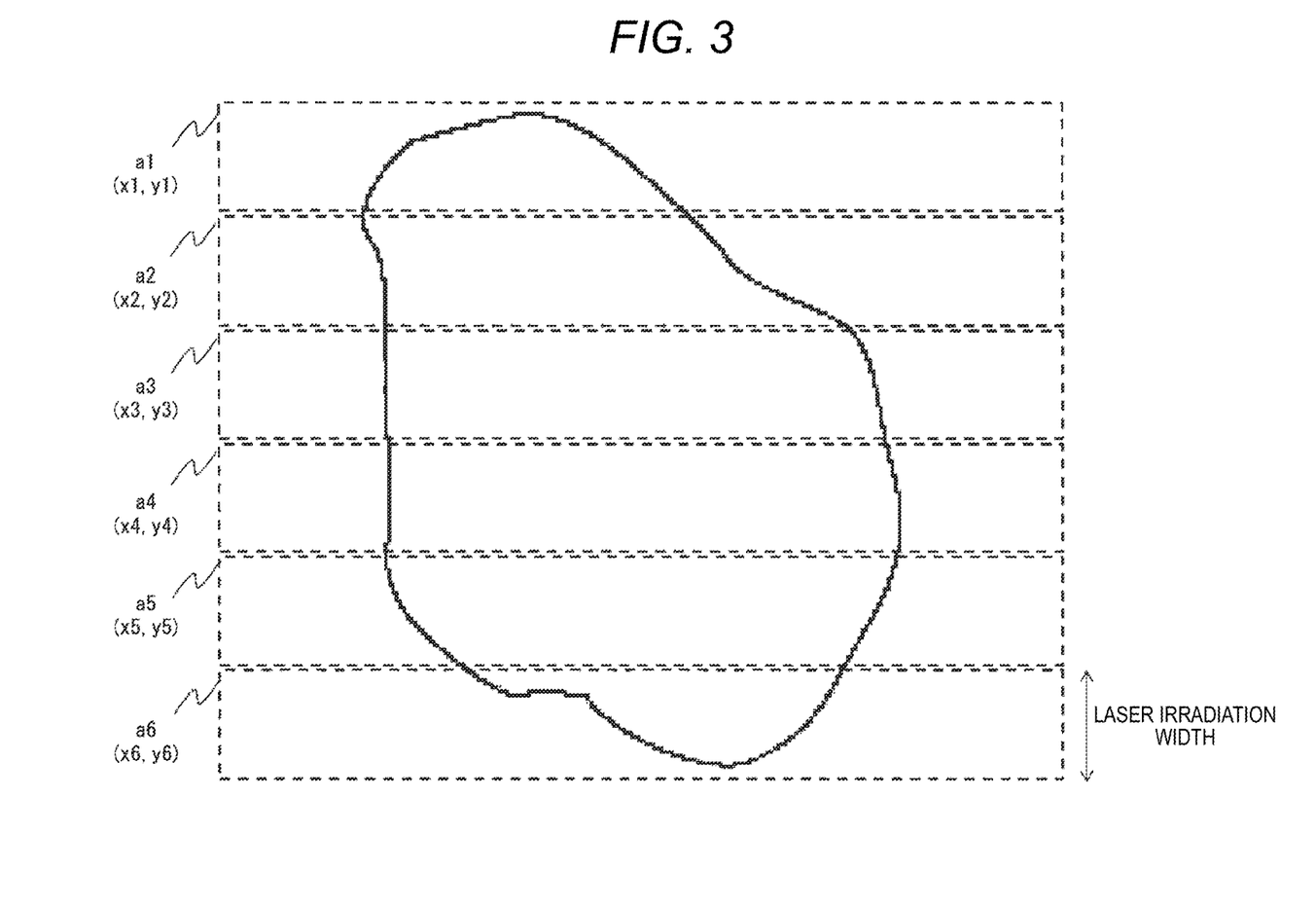
FIG. 3 is a diagram illustrating an image generation by a particle image generating section of the analyzing system.

FIG. 3 is a diagram illustrating an image generation by the particle image generating section 16. In FIG. 3, in order to facilitate the description, the particle size and the like are shown in a simplified manner. The particle image generating section 16 receives the scattered light intensity information and fluorescent light intensity information which correspond to the irradiation width of the laser light. The particle image generating section 16 generates partial images a1 to a6 based on the scattered light intensity information and fluorescent light intensity information which correspond to the irradiation width of the laser light. Then, the particle image generating section 16 refers to coordinate information and combines the partial images a1 to a6 to generate a particle image.

Alternatively, the imaging cytometer 10 may be configured so as to include a forward-scattered light detector and a side-scattered light detector. In the alternative, the particle image generating section 16 generates a particle image based on the forward-scattered light intensity detected by the forward-scattered light detector, and the side-scattered light intensity detected by the side-scattered light detector, in addition to the backward-scattered light intensity detected by the backward-scattered light detecting section 14.

Referring again to FIG. 1, the particle position detecting section 17 acquires position information from a position detecting sensor (not shown in FIG. 1) which detects the position of the particle container 11. The position information acquired by the particle position detecting section 17 is information from which the irradiation position of the laser light can be identified, such as "the x-coordinate=x1, the y-coordinate=y1" (the upper left end of the particle container 11 is set as (0, 0)). The particle position detecting section 17 writes the detected irradiation position information of the laser light in the storage section 19.

The particle classification measuring section 18 acquires the particle image generated by the particle image generating section 16, and analyzes the particle image. Specifically, the particle classification measuring section 18 analyzes the particle image to calculate the particle measurement value, the particle ratio, and the like. For example, the particle measurement value is the number of CD4 positive lymphocytes in the imaging-object region, that of CD4 negative lymphocytes, or the like. The particle ratio is the ratio of the number of CD4 positive lymphocytes contained in the analyte sample to that of CD4 negative lymphocytes, the CD4/CD8 ratio, or the like. The particle classification measuring section 18 realizes the measuring processes by means of a usual counting process.

The particle classification measuring section 18 writes a result of the analysis and the particle image in the storage section 19. The storage section 19 stores various information obtained in the imaging cytometer 10. The storage section 19 is a secondary storage device such as a hard disk drive, but alternatively may be a device that is detachable from the imaging cytometer 10, such as a universal serial bus (USB) memory.

The communicating section 20 transmits the particle measurement value, particle ratio, particle image, and the like which are obtained in the above-described processes. For example, the communicating section 20 may be configured by various circuits and the like which conform to a wireless communication standard. Alternatively, the communicating section 20 may be physically connected to a communicating section 36 which will be described later, through a cable or the like. The communicating section 20 may transmit all of particle images, but, from the viewpoint of communication traffic, preferably transmits only images in a typical region containing a particle which is determined to be false positive by the particle classification measuring section 18.

Alternatively, data passing between the imaging cytometer 10 and the blood cell analyzing apparatus 30 may be performed by using a record medium such as a USB memory. The data passing may be realized by an operation in which the user visually checks a result of analysis performed by the imaging cytometer 10, and inputs the analysis result in the blood cell analyzing apparatus 30.

The particle container position controlling section 21 controls the position of the particle container 11. More specifically, the particle container position controlling section 21 controls the position of the particle container 11 so that the particle is irradiated a plurality of times by the laser light. The control of the position of the particle container 11 by the particle container position controlling section 21 will be described with reference to FIGS. 4A to 5D. FIGS. 4A to 4D are views showing a first example of the position control of the particle container position controlling section 21, and positions of the particle container 11 which are changed with time.

Figure 4A:
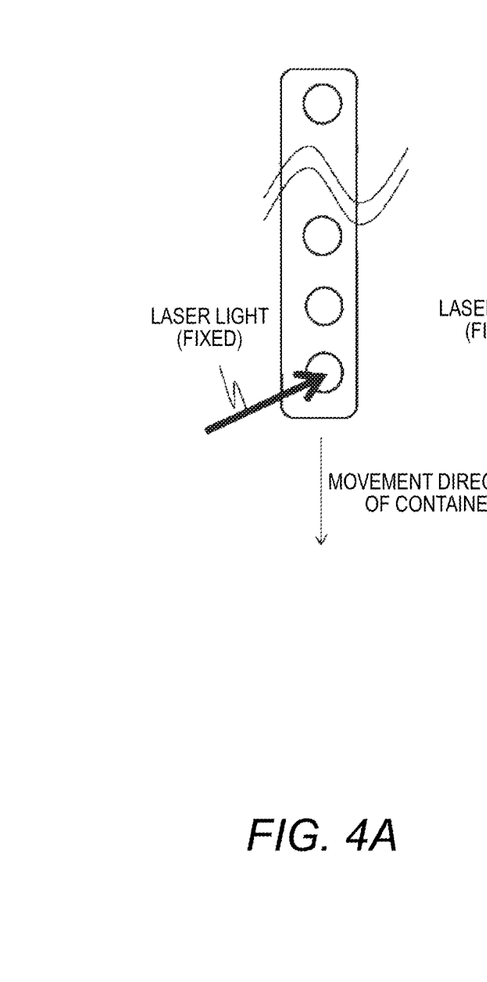
FIGS. 4A to 4D are diagrams illustrating a movement of an example of a particle container.
Figures 4B, 4C, 4D:
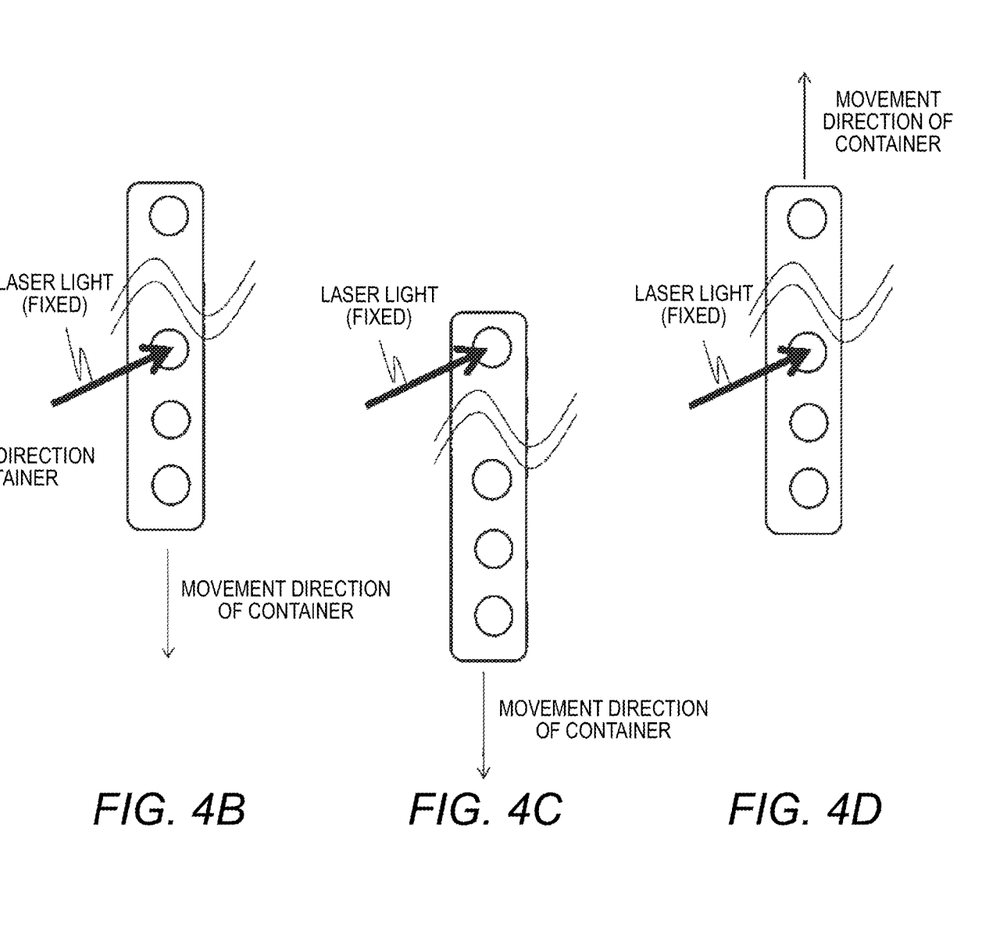

As illustrated, the irradiation position (absolute position) of the laser light which is emitted from the light source 13 is not changed. In FIG. 4A, the laser light irradiates a particle in the lowest portion of the particle container 11. FIG. 4B shows the irradiation state of the laser light after an elapse of a predetermined time period from the state of FIG. 4A. The particle container position controlling section 21 performed a control so that the particle container 11 is moved in the downward direction in the figure, and therefore a particle which is located at a higher position than that in FIG. 4A is irradiated. FIG. 4C shows the irradiation state of the laser light after an elapse of a predetermined time period from the state of FIG. 4B. Since the particle container position controlling section 21 performed a control so that the particle container 11 is moved in the downward direction in the figure, a particle which is located at the highest position is irradiated. FIG. 4D shows the irradiation state of the laser light after an elapse of a predetermined time period from the state of FIG. 4C. Since the particle container position controlling section 21 performed a control so that the particle container 11 is moved in the upward direction in the figure, a particle which is located at a lower position than that in FIG. 4C is irradiated.

As described above, the particle container position controlling section 21 moves the position of the particle container 11 so that particles contained in the particle container 11 are substantially uniformly irradiated with the laser light. The particle container position controlling section 21 repeats the reciprocal movement to perform a control so that each particle is irradiated a plurality of times. In FIGS. 4A to 4D, in order to simplify the description, the example in which the container is reciprocated in one direction has been described. Alternatively, the particle container position controlling section 21 may perform a control involving two-dimensional movement in the X- and Y-axis directions.

The movement of the particle container 11 may be realized by, for example, fixing the particle container 11 onto a placement plate which is not shown, and then moving the placement plate. In this case, a position detecting sensor (an encoder not shown in FIG. 1) is attached to the placement plate, and the position where the irradiation by the laser light is performed is detected by the position detecting sensor. Of course, the movement may be realized by another method.

Figure 5A:
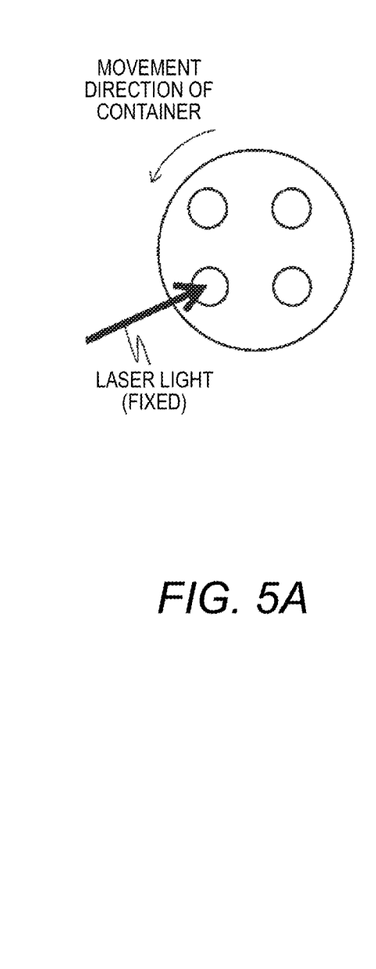
FIGS. 5A to 5D are diagrams illustrating a movement of another example of the particle container.
Figure 5B:
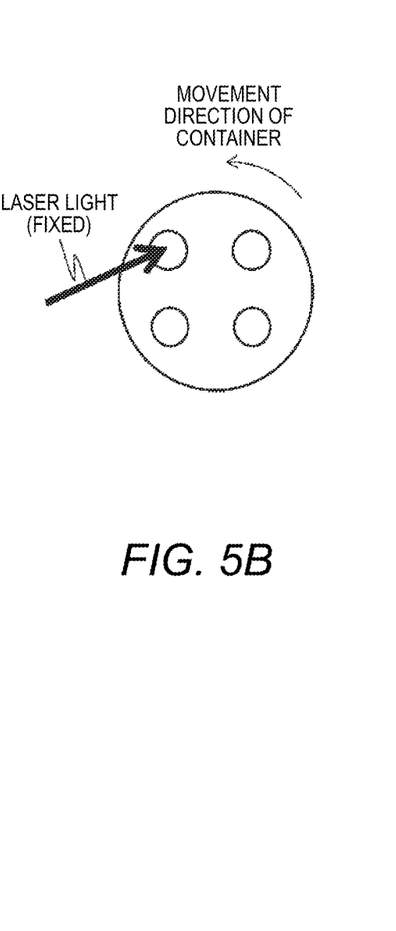
Figures 5C, 5D:
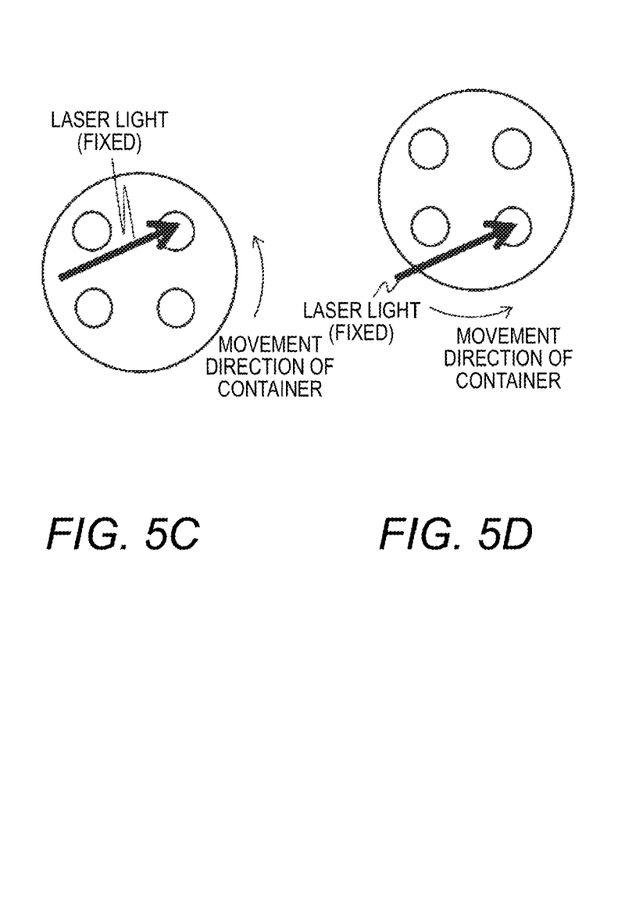

FIGS. 5A to 5D are views showing a second example of the position control of the particle container position controlling section 21, and positions of the particle container 11 which are changed with time. As illustrated, the irradiation position (absolute position) of the laser light which is emitted from the light source 13 is not changed. FIGS. 5A to 5D show positional relationships between the laser light and the particle container 11 after an elapse of a substantially predetermined time period. For example, FIG. 5B shows the irradiation state of the laser light on the particle container 11 after an elapse of a predetermined time period from the state of FIG. 5A. In order to enable particles to be substantially uniformly irradiated with the laser light, as illustrated, the particle container position controlling section 21 controls the position so that the particle container 11 makes a circle. The particle container position controlling section 21 performs a control so that particles are irradiated a plurality of times by repeating the circular movement.

In the imaging cytometer 10 of the exemplary embodiment, as described above, the analyte sample is placed in the particle container 11, and the particle container 11 is moved, so that particles are irradiated a plurality of times by the laser light.

The position control of FIGS. 5A to 5D is performed in the form of a circular movement, and the particle container 11 repeats the movement without temporally stopping. In the position control of FIGS. 4A to 4D, the container is moved in one direction, then temporally stopped, and thereafter moved in a substantially opposite direction. That is, the position control of FIGS. 4A to 4D is performed in the form of movements involving temporal stops. Therefore, the position control of FIGS. 5A to 5D enables the analysis to be performed at a high speed, and therefore is more preferable.

In the movements of FIGS. 4A to 5D, preferably, the particle container position controlling section 21 causes the particle container 11 to be moved so that particles contained in the container are substantially uniformly irradiated with the laser light. In order to enable particles to be irradiated substantially uniformly with the laser light, the movement (the reciprocal movement of FIGS. 4A to 4D, and the circular movement of FIGS. 5A to 5D) is preferably a constant-velocity movement. According to the configuration, particles are uniformly irradiated with the laser light, and can be analyzed more accurately.

Referring to FIG. 1, then, the configuration of the blood cell analyzing apparatus 30 will be described. The blood cell analyzing apparatus 30 includes a measuring section 31, an analyzing section 34, an output section 35, and a communicating section 36. The analyte sample that is the same as the analyte sample in the imaging cytometer 10 is loaded into the blood cell analyzing apparatus 30. For example, blood (analyte sample) taken from "subject A" is loaded into the imaging cytometer 10 and the blood cell analyzing apparatus 30. The blood cell analyzing apparatus 30 quantitatively analyzes particles contained in the analyte sample by at least one of an electrical resistance method and an optical analyzing method. As for the electrical resistance method and the optical analyzing method, see, Noriyuki Tatsumi, "Teaching Book on Instrumentation Technology—Basic Principle of Automated Blood Cell Analyzers", Uchudo Yagi Shoten, 2006, pp. 72-113.

The measuring section 31 analyzes blood cells of the analyte sample by using an electrical resistance method and optical analyzing method which are usually employed. As shown in FIG. 1, for example, the measuring section 31 has an electrical resistance measuring section 32 and an optical analysis measurement section 33. The configuration of FIG. 1 is a mere example. The measuring section 31 may have only one of the electrical resistance measuring section 32 and the optical analysis measurement section 33. The measuring section 31 may be configured in another manner as far as the section can analyze the components of the analyte sample.

The electrical resistance measuring section 32 is a processing section which implements a technique that may be a "golden standard" for the method of measuring the volume. The electrical resistance measuring section 32 causes the analyte sample to flow through a narrow tube called "aperture", analyzes the kinds of particles based on the electrical resistance produced in the flow, and measures the respective numbers of blood cells. With respect to the configuration and principle of the electrical resistance measuring section 32, see, Noriyuki Tatsumi, "Teaching Book on Instrumentation Technology—Basic Principle of Automated Blood Cell Analyzers", Uchudo Yagi Shoten, 2006, pp. 72-86.

In the optical analysis measurement section 33, a light source (preferably, a laser light source) is finely narrowed to produce a fine flow path (flow cell) through which particles contained in the analyte sample are to flow in a row in a direction perpendicular to the direction of the laser light. The optical analysis measurement section 33 analyzes light at the timing when a particle passes through the intersection of the flow cell and the laser light, thereby measuring the feature amount of the cells and classifying them. With respect to the configuration and principle of the optical analysis measurement section 33, see, Noriyuki Tatsumi, "Teaching Book on Instrumentation Technology—Basic Principle of Automated Blood Cell Analyzers ", Uchudo Yagi Shoten, 2006, pp. 86-113.

Unlike the imaging cytometer 10, the measuring section 31 does not perform an image analysis, and therefore can measure a large number of particles. The measuring section 31 supplies measurement values of blood cells (e.g., measurement values of blood cells per 1 μL), blood cell ratio, information of abnormal cells, and the like which are acquired by the electrical resistance method and the optical analyzing method, to the analyzing section 34 and a storage section (not shown).

The communicating section 36 is a communication interface with the imaging cytometer 10, and configured by circuits and the like which implement a wireless communication standard or the like. The communicating section 36 supplies the particle measurement value, particle ratio, particle image, and the like which are acquired from the imaging cytometer 10, to the analyzing section 34 and the output section 35.

At least one of the information (the particle measurement value, the particle ratio, the particle image, and the like) which is related to the particle analysis, and which is acquired by the imaging cytometer 10, and the information (the blood cell measurement value (e.g., measurement values of blood cells per 1 μL), the blood cell ratio, information of abnormal cells, and the like) which is related to the particle analysis, and which is acquired by the measuring section 31 are input to the analyzing section 34. The analyzing section 34 produces a new analysis report by using these sets of information, or controls the analyzing system 1 by using a result of an analysis of the information (various information supplied from the imaging cytometer 10, and various information supplied from the measuring section 31). Hereinafter, examples of operations performed by the analyzing section 34 will be described.

The analyzing section 34 produces a new analysis report by using the various information supplied from the imaging cytometer 10, and the various information supplied from the measuring section 31. Hereinafter, the operation will be described in detail with a specific example.

In the following, calculations of various parameters related to human immunodeficiency virus (HIV) infection will be described as an example. In follow-up of HIV infection, it is useful to refer to the absolute number of CD4 positive lymphocytes, the CD4/CD8 ratio, the proportion of CD4 positive lymphocytes in lymphocytes, the number of neutrophils, the number of platelets, and the like (see, e.g., "5. HIV Kansensho no Keika Kansatsu", api-net.jfap.or.jp/library/MeaRelDoc/03/htmls/doc_03_01_05.htm, accessible as of Jun. 20, 2014). Here, parameters of a healthy person have the following values (juntendo.ac.jp/hospital/support/rinsyo_kensabu/patient14.html, accessible as of Jun. 20, 2014):
the number of white blood cells (male)=3.9 to $9.7 \times 10^9$/L,
the number of white blood cells (female)=3.6 to $9.7 \times 10^9$/L,
neutrophils (Seg+Band)=37 to 72%,
lymphocytes (Lympho)=25 to 48%,
the number of lymphocytes=about 2000 particles/µL,
the number of CD4 positive lymphocytes=about 700 to about 1300 particles/µL, and
the CD4/CD8 ratio=1.0 to 2.0.

Here, the absolute number of CD4 lymphocytes per unit amount (per 1 µL) cannot simply be calculated by a single processing by the imaging cytometer 10 or the blood cell analyzing apparatus 30. Here, an example of calculating absolute number (particle amount) of a specific parameter per unit amount (per 1 µL) such as CD4 positive lymphocytes per unit amount will be described.

Normal Case

It is assumed that the following information regarding particle ratios is input from the imaging cytometer 10 in the analyzing section 34:
the percentage of CD4 positive lymphocytes=40%,
the percentage of CD8 positive lymphocytes=30%,
CD4/CD8=1.33333,
CD4/CD45=12%, and
CD8/CD45=8%.

It is further assumed that the following information regarding particle measurement values is input from the measuring section 31 in the analyzing section 34:
WBC (the number of white blood cells)=6000 particles/µL, and
the number of lymphocytes=1800 particles/µL.

The analyzing section 34 obtains the particle amount per unit amount of the analyte sample (e.g., the absolute number of CD4 positive lymphocytes per 1 µL, and the absolute number of CD8 positive lymphocytes per 1 µL) based on the above-described information by the following multiplication expressions:

$CD4$=6000 particles/µL×(1800/6000)×0.4=720 (particles/µL), and $CD8$=6000 particles/µL×(1800/6000)×0.3=540 (particles/µL).

The above numbers of CD4 and CD8 are determined to be within the above-described normal range. The analyzing section 34 supplies the calculated number of CD4 positive lymphocytes per 1 µL, and that of CD8 positive lymphocytes per 1 µL in the form of an analysis report to the output section 35. Preferably, the analysis report includes also information which is acquired singly by the imaging cytometer 10 and the blood cell analyzing apparatus 30 (e.g., the absolute number of neutrophils per unit amount and the like).

Abnormal Case

It is assumed that the following information regarding particle ratios is input from the imaging cytometer 10 in the analyzing section 34:
the percentage of CD4 positive lymphocytes=20%,
the percentage of CD8 positive lymphocytes=30%,
CD4/CD8=0.66667,
CD4/CD45=6%, and
CD8/CD45=9%.

It is further assumed that the following information regarding particle measurement values is input from the measuring section 31 in the analyzing section 34:
WBC (the number of white blood cells)=5000 particles/µL, and
the number of lymphocytes=1500 particles/µL.

The analyzing section 34 obtains the particle amount per unit amount of the analyte sample (e.g., the absolute number of CD4 positive lymphocytes per 1 µL, and the absolute number of CD8 positive lymphocytes per 1 µL) based on the above-described information by the following multiplication expressions:

$CD4$=5000 particles/µL×(1500/5000)×0.2=300 (particles/µL), and $CD8$=5000 particles/µL×(1500/5000)×0.3=450 (particles/µL).

The above numbers of CD4 and CD8 are determined not to be within the above-described normal range (i.e., to be abnormal). The analyzing section 34 supplies the calculated number of CD4 positive lymphocytes per 1 µL, and that of CD8 positive lymphocytes per 1 µL in the form of an analysis report to the output section 35.

Alternatively, the analyzing section 34 may detect various abnormal states by using the calculated absolute number of a specific parameter (such as the number of CD4 ositive lymphocytes) per unit amount. In the case where the number of CD4 positive lymphocytes is not within the normal range, for example, the analyzing section 34 sets a flag of reduction of the absolute value of CD4 or the like, and informs the user of the situation through the output section 35. Alternatively, the analyzing section 34 may detect an abnormality while considering a plurality of parameters. In the case where the number of CD4 positive lymphocytes and that of CD8 positive lymphocytes are within the normal range, but the two numbers are close to the outside of the normal rage, for example, the analyzing section 34 may determine that an abnormality occurs.

Another example of operations that may be performed by the analyzing section 34 will be described with reference to the flowchart of FIG. 6. In the initial state of the operation, the imaging cytometer 10 does not operate, only the measuring section 31 of the blood cell analyzing apparatus 30 performs the measuring process, and a result of the measuring process is supplied to the analyzing section 34 (S11). In the case where abnormal cell information (information of an abnormality flag which is output from a usual blood cell analyzing apparatus) is supplied from the measuring section 31, the analyzing section 34 detects that there is a possibility that the analyte sample is in an abnormal state (a state where the subject is suspected to suffer from any disease). Moreover, the analyzing section 34 detects an abnormal state also by comparing various information (e.g., the numbers of platelets and red blood cells per unit amount) supplied from the measuring section 31 with reference information (e.g., the normal ranges of the parameters).

If an abnormal state is not detected (S12: No), the analyzing section 34 outputs the result of the measuring process in the measuring section 31 to the output section 35, without causing the imaging cytometer 10 to perform analysis (detection of backward scattered light, that of fluorescent light, and the like), and end the process (S15).

By contrast, if an abnormal state is detected (S12: Yes), the analyzing section 34 transmits instructions for analysis to the imaging cytometer 10, thereby causing an analyte sample acquired from the same subject to be analyzed (S13). Then, the analyzing section 34 acquires various information (e.g., the particle measurement value, the particle ratio, and the particle image) acquired by the imaging cytometer 10, through the communicating sections (20, 36) (S14), and causes the output section 35 to output the acquired various information. After receiving the various information (such as the particle measurement value, the particle ratio, and the particle image) from the imaging cytometer 10, the analyzing section 34 may perform the operation described above (e.g., the calculation of the number of CD4 positive lymphocytes in 1 μL) and produce/output an analysis report.

The operation example of the analyzing section 34 has been described. Referring again FIG. 1, the output section 35 outputs the analysis report, particle image, and the like which are produced by the analyzing section 34. Here, the output includes display of the analysis result on a display device (not shown) of the blood cell analyzing apparatus 30, printing of the analysis result by an incorporated printer (not shown), and the like.

As a result of the above-described analysis related to HIV infection, for example, the output section 35 outputs the number of CD4 positive lymphocytes in 1 μL which is calculated in the above-described process, and an image of a false positive particle, in addition to the numbers of neutrophils and platelets which are acquired by the blood cell analyzing apparatus 30 by using the electrical resistance method or the optical analyzing method, by printing them on the same report sheet. Preferably, the output section 35 may further output the particle image (particularly, a morphology image of a particle which is determined to be false positive) received from the imaging cytometer 10, on the same report sheet. Therefore, the user can know both the particle morphology information and the particle count information.

Then, effects of the analyzing system 1 of the exemplary embodiment will be described. A conventional flow cytometer is superior in quantitatively analyzing a large number of particles, but has a problem in that it is difficult to obtain detailed information of the particle morphology. On the other hand, in a general imaging cytometer, detailed information of the particle morphology can be obtained, but there is a problem in that the processing speed is low and it is difficult to obtain a sufficient amount of statistics.

The analyzing system 1 according to one or more exemplary embodiments of the present invention has a configuration that has the advantages of both flow cytometer and imaging cytometer. More specifically, the imaging cytometer 10 acquires detailed information (such as the particle measurement value and the particle ratio) by imaging the particles, and the blood cell analyzing apparatus 30 performs a detailed quantitative analysis. By combining the processings of the two apparatuses are combined, the analyzing system 1 can acquire detailed information which cannot be acquired by a conventional apparatus and perform a flexible test.

For example, the analyzing section 34 produces the analysis report by using results of analyses which are performed by the imaging cytometer 10 and the blood cell analyzing apparatus 30. When referring to the analysis report, the user can refer to information (in the above-described example, the number of CD4 positive lymphocytes per 1 μL) which cannot be acquired by using only one of a flow cytometer and an imaging cytometer.

Figure 6:
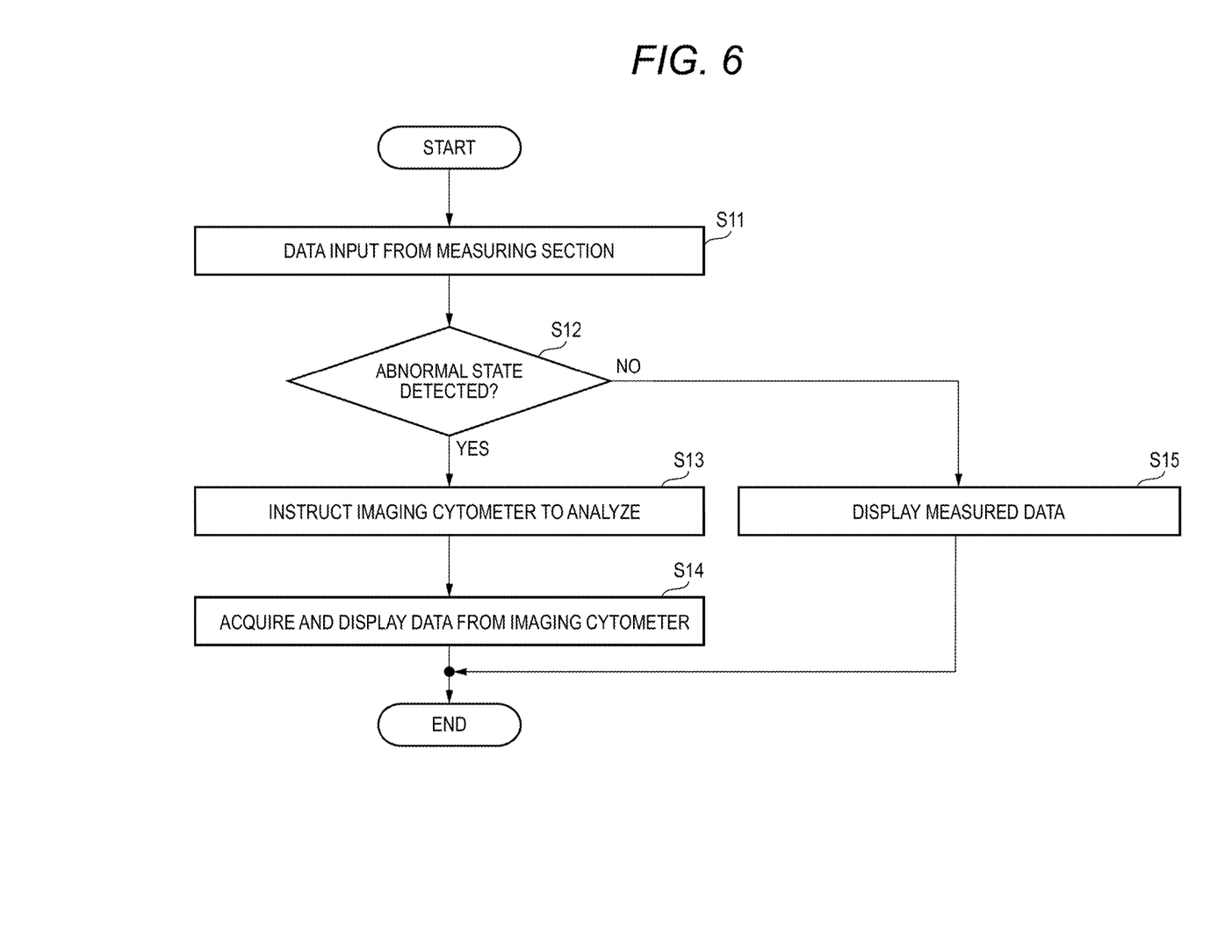
FIG. 6 is a flowchart of operations performed by an analyzing section of the analyzing system.

As shown in FIG. 6, a flexible system control such as that where only an analyte sample in which an abnormality is detected by the blood cell analyzing apparatus 30 is further subjected to the measurement by the imaging cytometer 10 is enabled. The imaging cytometer 10 is operated only in the case of necessity, and therefore this leads also to reduction of medical costs.

In the case of a particle having a small size, when the particle is irradiated with laser light, as described above, backward scattered light is largely produced (FIG. 2). The imaging cytometer 10 is configured so as to include the backward-scattered light detecting section 14. Therefore, the imaging cytometer 10 can correctly detect even a minute particle, a broken red blood cell, and the like.

Next, also effects of the imaging cytometer 10 in the case where it is independently used will be described. The particle container position controlling section 21 moves the particle container 11 so that the position irradiated with the laser light is changed. For example, the particle container position controlling section 21 moves the particle container 11 so that the particle container 11 performs a reciprocal movement (FIGS. 4A to 4D), or a circular movement (FIGS. 5A to 5D). According to the configuration, a particle is irradiated a number of times with the laser light, and the minimum sensitivity for particle detection can be raised. That is, the above-described imaging cytometer 10 can correctly detect even a minute particle or the like which, in a usual flow cytometer, cannot be accurately detected by one laser light irradiation.

As described above, the movement of the particle container 11 is preferably performed by a circular movement as shown in FIGS. 5A to 5D. According to the configuration, the analysis can be performed while the particle container 11 is continued to be moved (without temporally stopping), and therefore can be more quickly ended.

The particle image generating section 16 generates partial images (a1 to a6 in FIG. 3) based on the scattered light intensity and the fluorescent light intensity, and combines the partial images together to generate a larger image. That is, the particle image generating section 16 detects a particle by performing a scanning process. Although the partial images generated by the scanning are relatively rough images (low-quality image), the partial images can be generated quicker than a general imaging. According to the configuration, the imaging cytometer 10 of the exemplary embodiment can deal with a larger number of particles as compared with a cytometer having a general image producing function. In other words, the imaging cytometer 10 has a wide processing target range, and therefore can detect particles even when the number of particles is small. Since an imaging by scanning is quicker than a general imaging processing, the imaging cytometer 10 can promptly calculate the particle ratio and the like.

Figure 7:
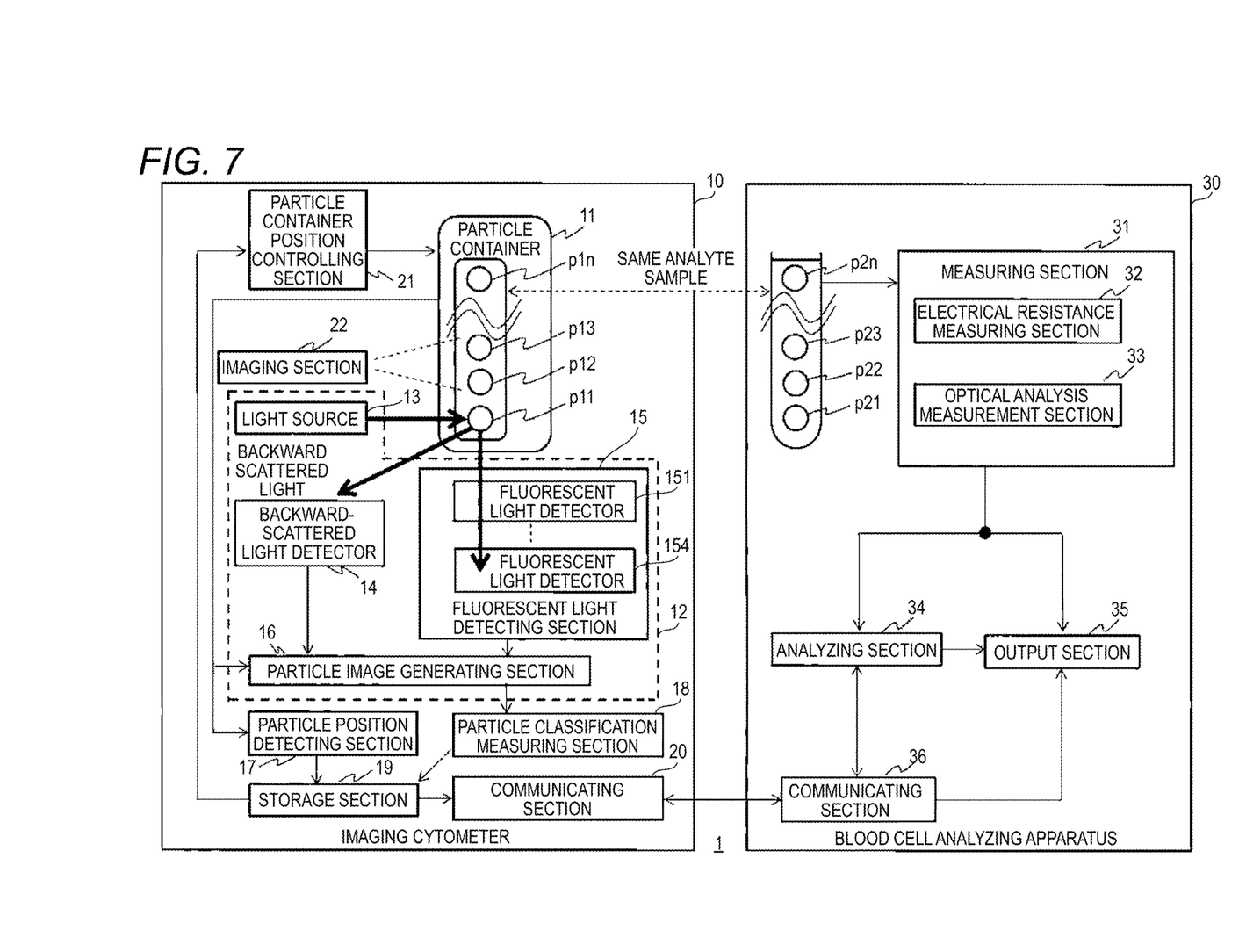
FIG. 7 is a block diagram of a configuration of an analyzing system according to another exemplary embodiment of the present invention.

FIG. 7 shows an analyzing system 1 according to another exemplary embodiment of the present invention. In FIG. 7, the sections denoted by the same reference numerals and names as those of FIG. 1 perform the processing that are identical with those of the exemplary embodiment of FIG. 1 unless otherwise described. This applies to other exemplary embodiments which will be described later. The analyzing system 1 of FIG. 7 is different from the e analyzing system 1 of FIG. 1 in that the system further has an imaging section 22 (a second imaging section) in the imaging cytometer 10

The imaging section 22 takes an image of the particle state in the particle container 11 to acquire a particle image. The imaging section 22 is an imaging device (camera) that can generate a particle image with higher quality than an image generated by the particle image generating section 16. That is, the imaging section 22 acquires an image in which the resolution is higher than that of a particle image generated by the particle image generating section 16. The imaging section 22 may have usual optical members, but preferably has a sufficient function of imaging a particle.

The imaging timing of the imaging section 22 may be the timing at which the particle classification measuring section 18 detects an abnormality (positive cell), or that at which a mode change or imaging instructions are designated by the user through a button or the like on the housing. In the case where imaging is performed at the timing when an abnormality (positive cell) is detected, the imaging section 22 can perform imaging after the position information of the imaging target is acquired from the storage section 19.

As described above, the particle image generating section 16 generates partial images by scanning, and combines the partial images together to generate an image from which the particle shape can be confirmed. Although the scanning can be performed at a high speed as described above, it is difficult to generate a high-quality image that accurately reproduces a shape of a particle. In contrast, in the imaging section 22, the number of particles that can be processed is small (the processing speed is low), but it is possible to obtain a high-quality image from which the shape of the particle can be accurately confirmed.

For example, the imaging section 22 can take a high-quality image showing the position of a cell which is determined to be false positive by the particle classification measuring section 18. When referring to the high-quality image, the user can know in detail the shape of the cell which is determined to be false positive.

Figure 8:
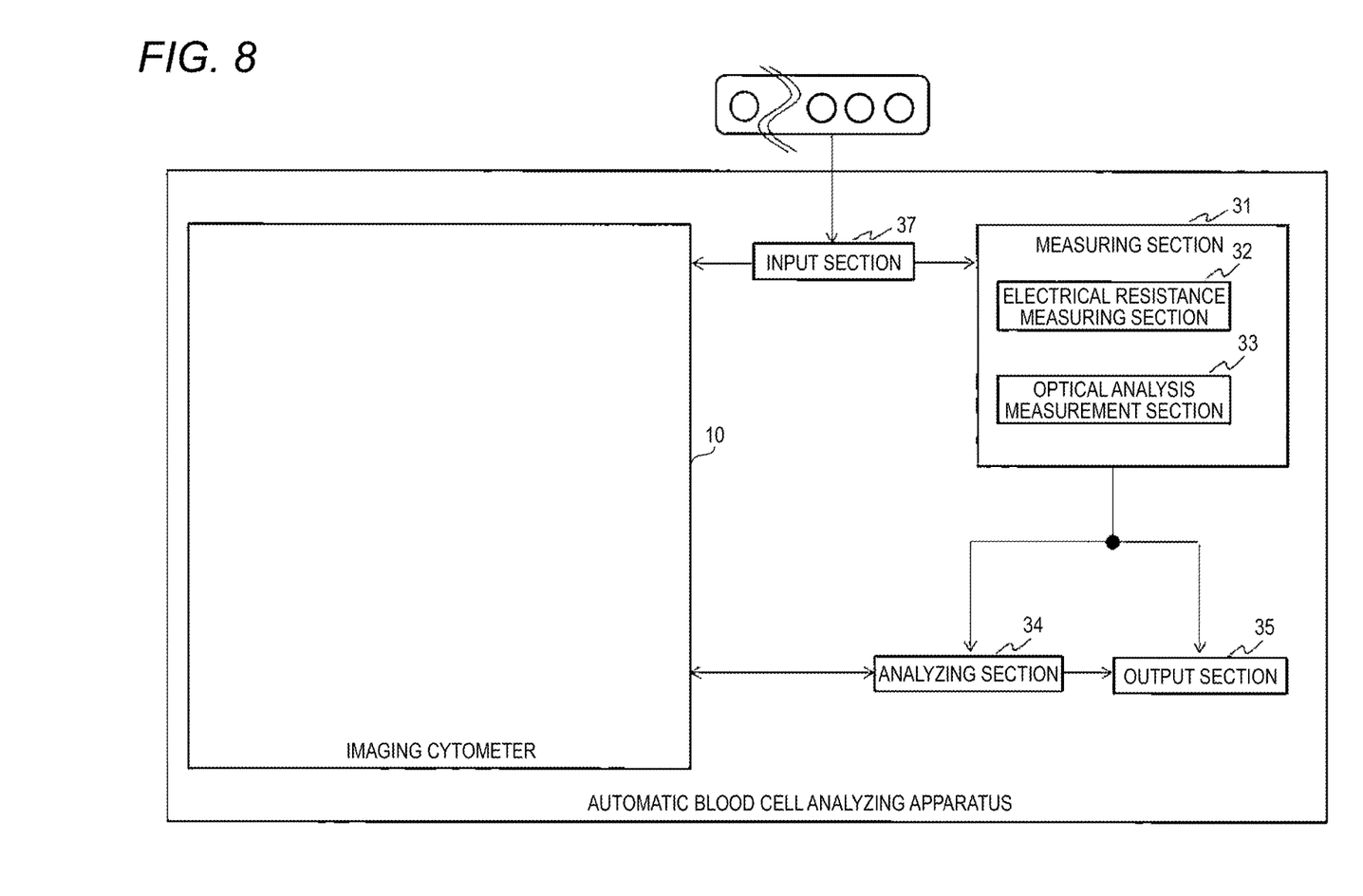
FIG. 8 is a block diagram of a configuration of a blood cell analyzing apparatus according to another exemplary embodiment of the present invention.

According to another exemplary embodiment of the present invention, the configuration of the imaging cytometer 10 described above is incorporated in the blood cell analyzing apparatus 30 as shown in FIG. 8 so that and the cytometer and the analyzing apparatus are configured as a single apparatus.

The blood cell analyzing apparatus 30 has a configuration in which the imaging cytometer 10 in Exemplary embodiment 1 or 2 is incorporated. Although not shown in the figure, the internal configuration of the imaging cytometer 10 may be identical with or equivalent to that shown in FIG. 1 or 7.

The user loads an analyte sample to be analyzed, into the blood cell analyzing apparatus 30. An input section 37 extracts a part of the loaded analyte sample, supplies the extracted part to the imaging cytometer 10, and supplies the remaining part of the analyte sample (or another part which is extracted from the analyte sample) to the measuring section 31. That is, the blood cell analyzing apparatus 30 extracts a part of the loaded analyte sample, uses the extracted part as the analysis target for the imaging cytometer 10, and uses the remaining part of the analyte sample (or another part which is extracted from the analyte sample) as the analysis target for the measuring section 31. The other process is identical with that of Exemplary embodiment 1.

In the exemplary embodiment, the imaging cytometer 10 and the blood cell analyzing apparatus 30 are integrated with each other, and therefore effects similar to those of Exemplary embodiment 1 can be attained by the single apparatus. The input section 37 extracts parts from the loaded analyte sample, and supplies the extracted parts to the imaging cytometer 10 and the measuring section 31, respectively. When the user loads only one time the analyte sample, therefore, it is possible to perform both the image-based analysis and the optical analysis (or the electrical-resistance-based analysis).

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

Figure 9:
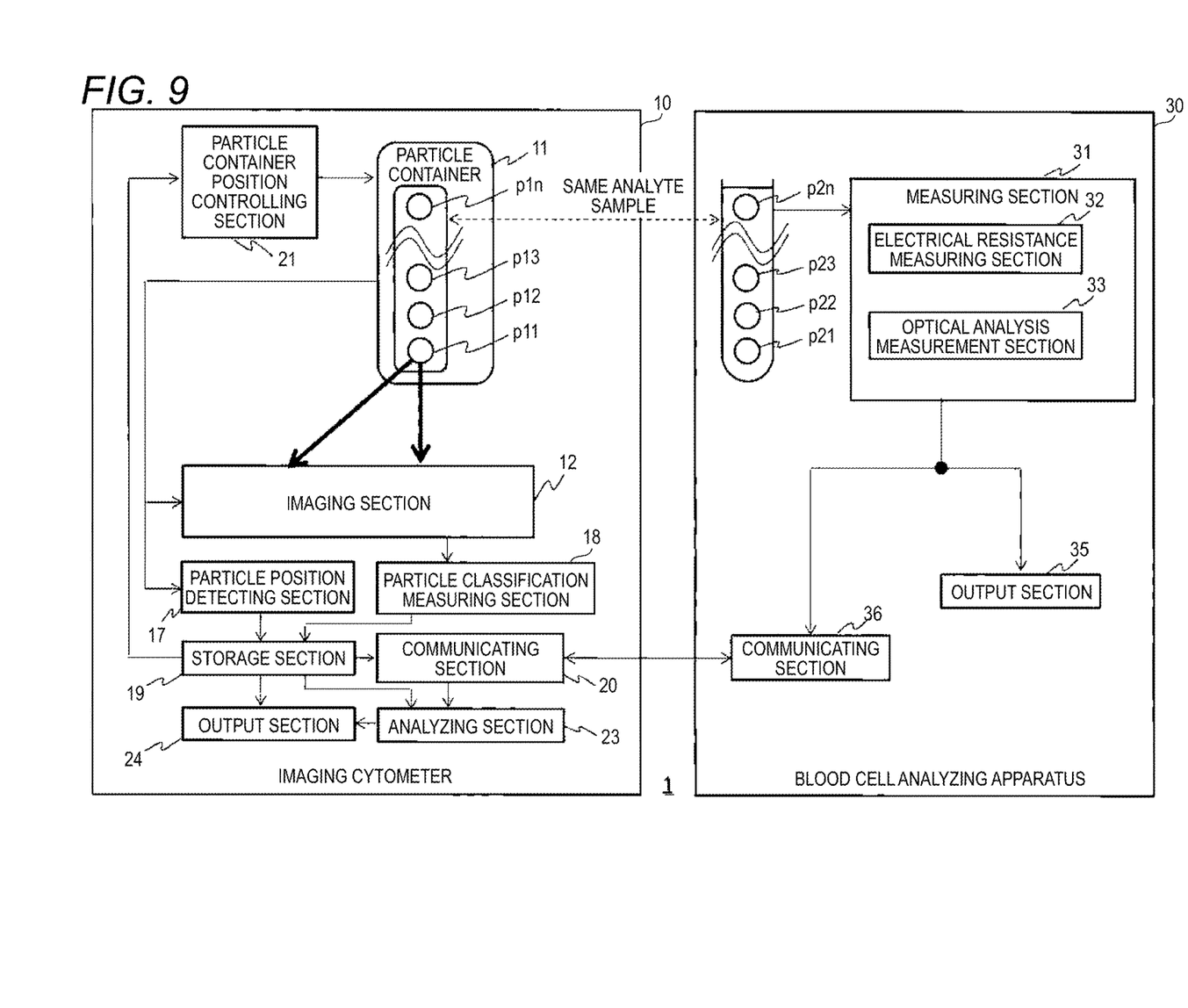
FIG. 9 is a block diagram of a configuration of an analyzing system according to another exemplary embodiment of the present invention.

In Exemplary embodiment 1 or 2, for example, a configuration may be possible where the function of the analyzing section 34 is in the imaging cytometer 10, and the imaging cytometer 10 calculates the above-described analysis report. FIG. 9 is a block diagram showing this configuration. Although, in FIG. 9, the internal configuration of the imaging section 12 is simplistically shown, the internal configuration may be equivalent to that sown in FIG. 1. As illustrated, an analyzing section 23 and an output section 24 exist in the imaging cytometer 10. The analyzing section 23 may be configured so as to operate in a similar manner as the analyzing section 34 of FIG. 1. That is, the analyzing section 23 may be configured to output an analysis report by using an image taken by the imaging section 12 of the imaging cytometer 10 and a result of a measurement by the measuring section 31 of the blood cell analyzing apparatus 30. The output section 24 outputs the analysis report produced by the analyzing section 23, by using an arbitrary technique (printing, displaying on the display device, or the like). Data passing between the two apparatuses may be performed in a wireless manner, or by using a storage medium such as a USB (Universal Serial Bus) memory. Alternatively, the data passing may be performed by manually input data in the imaging cytometer.

In the above description, the imaging section 12 detects the intensities of scattered light and fluorescent light, and generates an image based on the intensities. The manner of generating an image is not limited to this. The imaging section 12 may be configured as, for example, an imaging camera that can detect the particle ratio and the like at a high speed (a camera that operates at a higher speed than the imaging section 22 but inferior in image quality).

Figure 10:
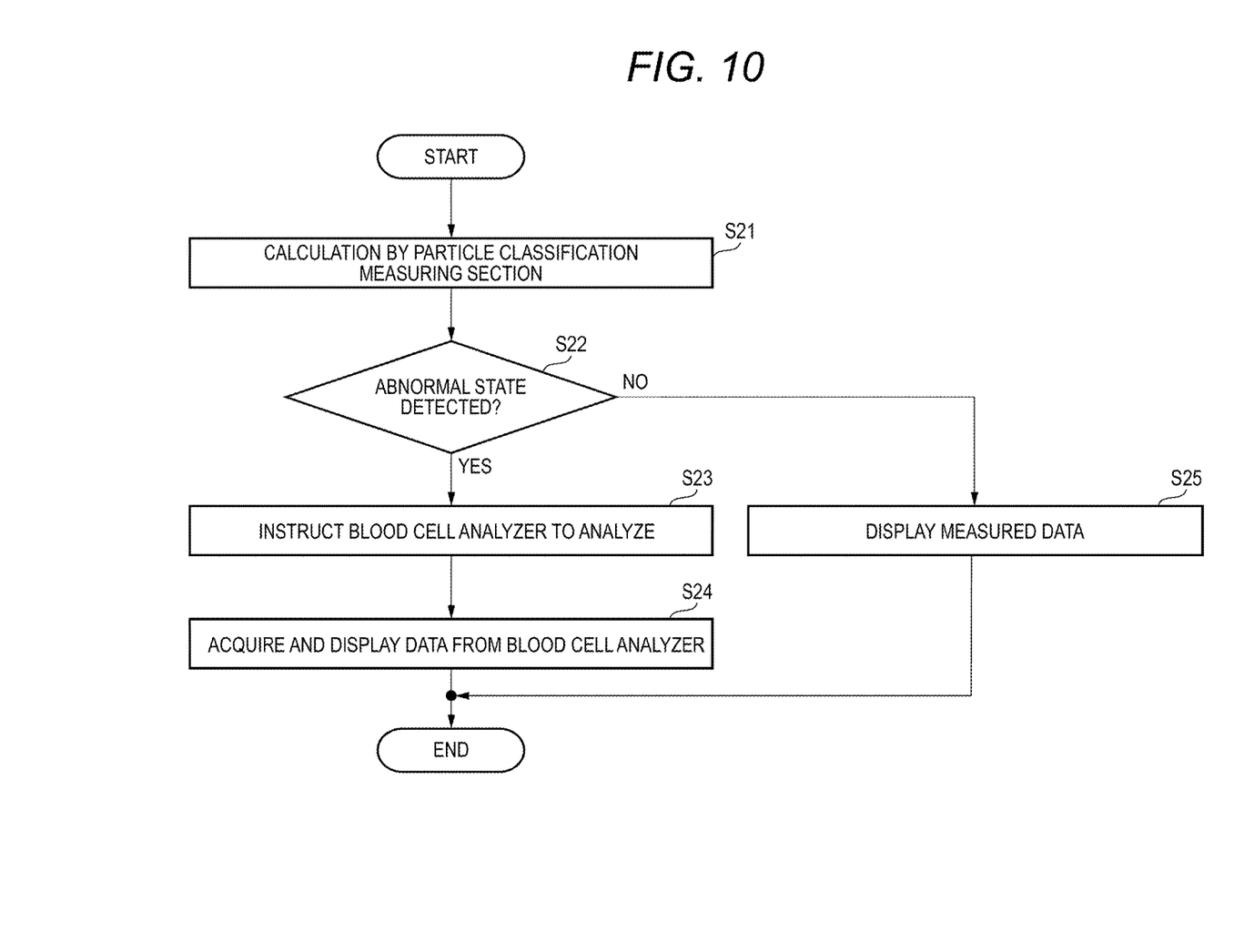
FIG. 10 is another flowchart of operations performed by the analyzing section.

In the operation example shown in FIG. 6, the blood cell analyzing apparatus 30 performs an analysis, and, in the case where an abnormality is detected, the imaging cytometer 10 performs an analysis. The invention is not limited to this. Referring to FIG. 10, an operation example in which the imaging cytometer 10 performs an analysis, and, in the case where an abnormality is detected, the blood cell analyzing apparatus 30 performs an analysis will be described.

The particle classification measuring section 18 calculates the particle ratio and the like based on images generated by the imaging section 12 (S21). If the calculated particle ratio and the like are not abnormal (S22: No), the information of the particle ratio and the like which are calculated by the particle classification measuring section 18 are output to the display device and the like of the imaging cytometer 10, and then the process is ended (S25).

If the calculated particle ratio or the like is abnormal (S22: Yes), the imaging cytometer 10 transmits instructions for an analysis, and the analysis result to the blood cell analyzing apparatus 30 (S23). The blood cell analyzing apparatus 30 performs an analysis on the same analyte sample, and the results of the analyses performed by the both apparatuses are output (S24).

What is claimed is:

1. An analyzing system comprising:
an imaging cytometer comprising a first communication interface, a particle container and a first imaging section, the first imaging section being configured to image a first set of particles contained in an analyte sample inside the particle container, thereby generating images of the first set of particles; and
a blood cell analyzing apparatus comprising a second communication interface connected to the first communication interface in a wired or wireless manner to allow communication between the imaging cytometer and the blood cell analyzing apparatus via the first communication interface and at least one of an electrical resistance measuring section and an optical analysis measurement section, the blood cell analyzing apparatus being configured to analyze a second set of particles contained in a flow of the analyte sample, the electrical resistance measuring section being configured to analyze the second set of particles based on electrical resistance produced in the flow, and the optical analysis measurement section being configured to analyze the second set of particles based on light directed toward the flow,
wherein the imaging cytometer or the blood cell analyzing apparatus comprises at least one processor and at least one non-transitory computer readable memory configured to:
cause the imaging cytometer to analyze generated images of the first set of particles to acquire first particle information;
cause the blood cell analyzing apparatus to analyze the second set of particles to acquire second particle information;
combine the first particle information and the second particle information via the first communication interface and the second communication interface;
produce a report of an analysis of the analyte sample based on the first particle information acquired by the imaging cytometer and the second particle information acquired by the blood cell analyzing apparatus; and
multiply a particle ratio acquired by the imaging cytometer by a particle measurement value per unit amount of the analyte sample acquired by the blood cell analyzing apparatus, to calculate an absolute number of a specific parameter per unit amount of the analyte sample, the particle ratio being a ratio of a number of CD4 positive lymphocytes contained in the analyte sample to a number of CD4 negative lymphocytes contained in the analyte sample, or a CD4/CD8 ratio.

2. The analyzing system according to claim 1, wherein the at least one processor and the at least one non-transitory computer readable memory are further configured to determine whether the calculated absolute number of the specific parameter per unit amount of the analyte sample is within a given range.

3. The analyzing system according to claim 1,
wherein the imaging cytometer further comprises a first communicating section configured to transmit a particle image to the blood cell analyzing apparatus, the particle image being an image of a particle contained in the analyte sample, and
wherein the blood cell analyzing apparatus further comprises a second communicating section configured to receive the particle image and an output section configured to output the particle image.

4. The analyzing system according to claim 1, wherein the first imaging section is configured to perform the imaging of the particle contained in the analyte sample based on an intensity of scattered light or fluorescent light that is obtained by irradiating the analyte sample with light.

5. The analyzing system according to claim 4, wherein the imaging cytometer further comprises a backward-scattered light detecting section configured to detect backward scattered light that is produced by irradiating the analyte sample with light.

6. The analyzing system according to claim 1, wherein the imaging cytometer further comprises a second imaging section configured to generate images of the first set of particles in the analyte sample.

7. The analyzing system according to claim 1, wherein the at least one processor and the at least one non-transitory computer readable memory are further configured to decide whether to cause the imaging cytometer to analyze the images based on the analysis on the analyte sample by the blood cell analyzing apparatus.

8. The analyzing system according to claim 1, wherein the at least one processor and the at least one non-transitory computer readable memory are further configured to decide whether to cause the blood cell analyzing apparatus to analyze the second set of particles based on the analysis on the analyte sample by the imaging cytometer.

9. The analyzing system according to claim 1, wherein the imaging cytometer is provided in the blood cell analyzing apparatus.

10. The analyzing system according to claim 1, wherein the at least one processor and the at least one non-transitory computer readable memory are further configured to calculate an absolute number of a first type of particles per unit amount of the analyte sample by multiplying a particle ratio, the ratio being a number of the first type of particles to a number of a second type of particles acquired by the imaging cytometer, by a number of the second type of particles per unit amount of the analyte sample acquired by the blood cell analyzing apparatus.

* * * * *

UNITED STATES PATENT AND TRADEMARK OFFICE
CERTIFICATE OF CORRECTION

PATENT NO.         : 10,436,699 B2
APPLICATION NO.    : 14/885432
DATED              : October 8, 2019
INVENTOR(S)        : Yutaka Nagai Page 1 of 1

It is certified that error appears in the above-identified patent and that said Letters Patent is hereby corrected as shown below:

In the Specification

Column 10, Line 35, "ositive" should read --positive--

Signed and Sealed this
Thirty-first Day of March, 2020

Andrei Iancu
*Director of the United States Patent and Trademark Office*